(12) United States Patent
Kamtekar

(10) Patent No.: US 11,600,785 B2
(45) Date of Patent: Mar. 7, 2023

(54) PHOTOACTIVE COMPOUND

(71) Applicant: Sumitomo Chemical Company Limited, Tokyo (JP)

(72) Inventor: Kiran Kamtekar, Godmanchester (GB)

(73) Assignee: Sumitomo Chemical Company Limited, Tokyo (JP)

( * ) Notice: Subject to any disclaimer, the term of this patent is extended or adjusted under 35 U.S.C. 154(b) by 494 days.

(21) Appl. No.: 16/712,315

(22) Filed: Dec. 12, 2019

(65) Prior Publication Data
US 2020/0194684 A1    Jun. 18, 2020

(30) Foreign Application Priority Data

Dec. 14, 2018 (GB) ...................... 1820384

(51) Int. Cl.
*C07D 495/22* (2006.01)
*H01L 51/00* (2006.01)
*H01L 51/42* (2006.01)
*H01L 27/30* (2006.01)
*H01L 51/44* (2006.01)

(52) U.S. Cl.
CPC ........ H01L 51/0071 (2013.01); C07D 495/22 (2013.01); H01L 51/0058 (2013.01); H01L 51/0068 (2013.01); H01L 51/4253 (2013.01); H01L 27/307 (2013.01); H01L 51/0007 (2013.01); H01L 51/0028 (2013.01); H01L 51/442 (2013.01)

(58) Field of Classification Search
CPC ........ C07D 495/22; H01L 51/42; H01L 51/00
USPC .................................. 549/41; 313/498, 504
See application file for complete search history.

(56) References Cited

FOREIGN PATENT DOCUMENTS

| CN | 107652304 A | 2/2018 |
|---|---|---|
| JP | 2015-189853 A | 11/2015 |
| WO | WO 2018/099492 A2 | 6/2018 |

OTHER PUBLICATIONS

GB 1820384.4, Jun. 12, 2019, Combined Search and Examination Report.
Combined Search and Examination Report for Application No. GB 1820384.4 dated Jun. 12, 2019.

*Primary Examiner* — Charanjit Aulakh
(74) *Attorney, Agent, or Firm* — Wolf, Greenfield & Sacks, P.C.

(57) ABSTRACT

A compound of formula (I):

EAG-EDG-EAG    (I)

wherein each EAG is an electron accepting group; and EDG is an electron-donating group of formula (IIa):

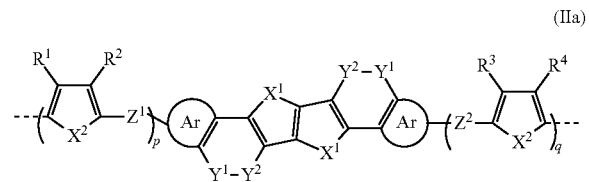

The compound of formula (I) may be used in a photosensitive layer of an organic photodetector wherein the photosensitive layer comprises the compound of formula (I) and an electron donor. A photosensor may comprise the organic photodetector and a light source, e.g. a near infra-red light source.

18 Claims, 1 Drawing Sheet

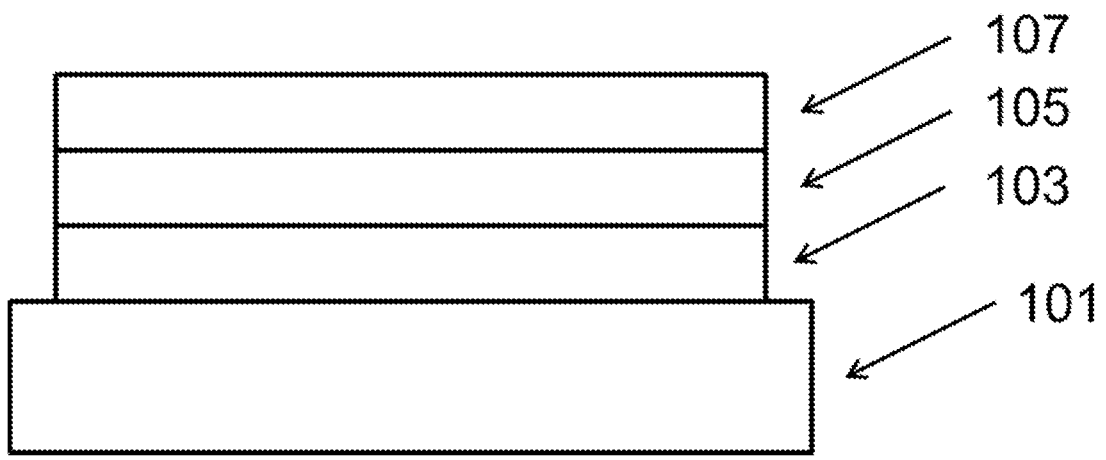

PHOTOACTIVE COMPOUND

RELATED APPLICATIONS

This application claims foreign priority benefits under 35 U.S.C. § 119(a)-(d) or 35 U.S.C. § 365(b) of British application number GB 1820384.4, filed Dec. 14, 2018, the entirety of which is incorporated herein.

BACKGROUND

Embodiments of the present disclosure relate in particular to photoactive compounds for use in organic photodetectors.

A range of organic electronic devices comprising organic semiconductor materials are known, including organic light-emitting devices, organic field effect transistors, organic photovoltaic devices and organic photodetectors (OPDs).

WO2018099492A2 discloses an OPD having a photoactive layer that contains a small molecule acceptor and a conjugated copolymer electron donor having donor and acceptor units.

CN107652304 discloses an organic solar cell that contains a fused-ring non-fullerene acceptor material.

Liu et al, "Ternary Blend Strategy for Achieving High-Efficiency Organic Solar Cells with Nonfullerene Acceptors Involved" Adv. Func. Mat., 2018, 28 (29), 1-20, discloses non-fullerene acceptor COi8DFIC.

He et al, "A-D-A small molecule acceptors with ladder-type arenes for solar cell" J. of Mat. Chem. A, 2018, 6, 8839-8854, discloses COi8DFIC with an ultranarrow bandgap of 1.26V.

Xu et al "The progress and prospects of non-fullerene acceptors in ternary blend organic solar cells" Mat. Horizons, 2018, 5, 206-221, discloses COi8DFIC.

Xiao et al, "26 mA cm-2 Jsc from organic solar cells with a low-bandgap nonfullerene acceptor" Sci. Bull., 2017, 62, 1494, discloses the A-D-A non-fullerene acceptor, COi8DFIC which has a narrow optical bandgap of 1.26 eV.

Xiao et al, "Ternary organic solar cells offer 14% power conversion efficiency" Sci. Bull., 2017, 62, 1562, discloses COi8DFIC in a polyer:fullerene:non-fullerene ternary solar cell.

Li et al, "Thermostable single-junction organic solar cells with a power conversion efficiency of 14.62%" Sci. Bull., 2018, 63, 340, discloses the low-bandgap non-fullerene acceptor COi8DFIC.

SUMMARY

A summary of aspects of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects and/or a combination of aspects that may not be set forth.

Embodiments of the present disclosure provide a compound of formula (I):

$$\text{EAG-EDG-EAG} \tag{I}$$

wherein each EAG is an electron accepting group; and EDG is an electron-donating group of formula (IIa):

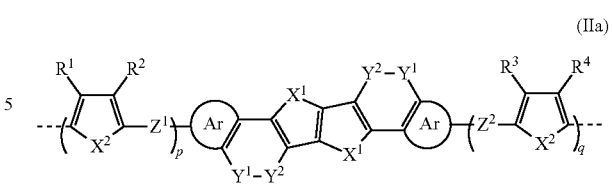

wherein:
each $X^1$ and $X^2$ is independently O, S or Se;
one of $Y^1$ and $Y^2$ is O and the other is $CR^5R^6$;
each $R^5$ and $R^6$ is independently H or a substituent;
Ar independently in each occurrence is a monocyclic or polycyclic aromatic or heteroaromatic group;
$Z^1$ is a direct bond or, together with $R^2$, forms an aromatic or heteroaromatic group $Ar^1$;
$Z^2$ is a direct bond or, together with $R^3$, forms an aromatic or heteroaromatic group $Ar^2$;
$R^1$ and $R^4$ are each independently H, a substituent or a divalent group bound to the EAG;
$R^2$ and $R^3$, independently in each occurrence is H or a substituent;
p is 0, 1, 2 or 3 and q is 0, 1, 2 or 3 with the proviso that at least one of p and q is at least 1; and
---- is a point of attachment to the EAG.

In some embodiments, there is provided a composition containing an electron-accepting (n-type) compound as described herein and an electron donor (p-type) compound.

In some embodiments there is provided a formulation comprising a composition as described herein dissolved or dispersed in one or more solvents.

In some embodiments there is provided an organic photodetector comprising: an anode; a cathode; and a photosensitive organic layer disposed between the anode and cathode. The photosensitive organic layer comprises an electron donor and an electron acceptor of formula (I).

In some embodiments, there is provided a method of forming an OPD as described herein comprising formation of the photosensitive organic layer over one of the anode and cathode and formation of the other of the anode and cathode over the photosensitive organic layer.

In some embodiments, there is provided a circuit comprising an organic photodetector as described herein, and at least one of a voltage source for applying a reverse bias to the organic photodetector and a device configured to measure photocurrent generated by the photodetector.

In some embodiments there is provided a photosensor comprising a light source and an OPD as described herein configured to detect light emitted from the light source.

In some embodiments, there is provided a method of determining the presence and/or concentration of a target material in a sample, the method comprising illuminating the sample and measuring a response of an OPD as described herein which is configured to receive light emitted from the sample upon illumination.

DESCRIPTION OF DRAWINGS

The disclosed technology and accompanying FIGURES describe some implementations of the disclosed technology.

FIG. 1 illustrates an organic photodetector according to an embodiment of the invention.

The drawings are not drawn to scale and have various viewpoints and perspectives. The drawings are some implementations and examples. Additionally, some components and/or operations may be separated into different blocks or combined into a single block for the purposes of discussion of some of the embodiments of the disclosed technology. Moreover, while the technology is amenable to various modifications and alternative forms, specific embodiments have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, electromagnetic, or a combination thereof. Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while some aspect of the technology may be recited as a computer-readable medium claim, other aspects may likewise be embodied as a computer-readable medium claim, or in other forms, such as being embodied in a means-plus-function claim.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

FIG. 1 illustrates an OPD according to some embodiments of the present disclosure. The OPD comprises a cathode 103, an anode 107 and a bulk heterojunction layer 105 disposed between the anode and the cathode. The OPD may be supported on a substrate 101, optionally a glass or plastic substrate.

FIG. 1 illustrates an arrangement in which the cathode is disposed between the substrate and the anode. In other embodiments, the anode may be disposed between the cathode and the substrate.

The bulk heterojunction layer comprises a mixture of an electron acceptor and an electron donor. In some embodiments, the bulk heterojunction layer consists of the electron acceptor and the electron donor. In some embodiments, the bulk heterojunction layer comprises a further electron acceptor other than the electron acceptor of formula (I). Optionally, the further electron acceptor is a fullerene.

Each of the anode and cathode may independently be a single conductive layer or may comprise a plurality of layers.

The OPD may comprise layers other than the anode, cathode and bulk shown in FIG. 1. In some embodiments, a hole-transporting layer is disposed between the anode and the bulk heterojunction layer. In some embodiments, an electron-transporting layer is disposed between the cathode and the bulk heterojunction layer. In some embodiments, a work function modification layer is disposed between the bulk heterojunction layer and the anode, and/or between the bulk heterojunction layer and the cathode.

In use, the photodetectors as described in this disclosure may be connected to a voltage source for applying a reverse bias to the device and/or a device configured to measure photocurrent. The voltage applied to the photodetectors may be variable. In some embodiments, the photodetector may be continuously biased when in use.

In some embodiments, a photodetector system comprises a plurality of photodetectors as described herein, such as an image sensor of a camera.

In some embodiments, a sensor may comprise an OPD as described herein and a light source wherein the OPD is configured to receive light emitted from the light source.

In some embodiments, the light from the light source may or may not be changed before reaching the OPD. For example, the light may be filtered, down-converted or up-converted before it reaches the OPD.

The bulk heterojunction layer may contain an electron acceptor (n-type) compound of formula (I):

EAG-EDG-EAG (I)

wherein each EAG is an electron accepting group; and EDG is an electron-donating group of formula (IIa):

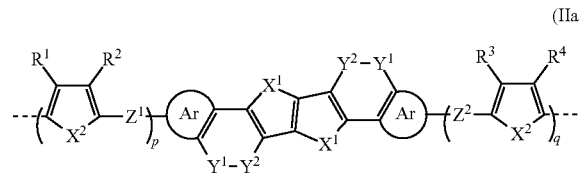

(IIa)

wherein:
each $X^1$ and $X^2$ is independently O, S or Se;
one of $Y^1$ and $Y^2$ is O and the other is $CR^5R^6$ wherein each $R^5$ and $R^6$ is independently H or a substituent;
Ar independently in each occurrence is a monocyclic or polycyclic aromatic or heteroaromatic group;
$Z^1$ is a direct bond or, together with $R^2$, forms an aromatic or heteroaromatic group Ar;
$Z^2$ is a direct bond or, together with $R^2$, forms an aromatic or heteroaromatic group $Ar^2$;
$R^1$ and $R^4$ are each independently H, a substituent or a divalent group bound to the EAG;
$R^2$ and $R^3$, independently in each occurrence is H or a substituent;
p is 0, 1, 2 or 3 and q is 0, 1, 2 or 3 with the proviso that at least one of p and q is at least 1; and
---- is a point of attachment to the EAG.

replaced with O, S, CO or COO; u is 0 or 1; $Ar^4$ in each occurrence is independently an aromatic or heteroaromatic group which is unsubstituted or substituted with one or more substituents; and v is at least 1, optionally 1, 2 or 3.

In some embodiments $C_{1-12}$ hydrocarbyl may be $C_{1-12}$ alkyl; unsubstituted phenyl; and phenyl substituted with one or more $C_{1-6}$ alkyl groups.

In some embodiments u is 0 and v is 1.

In some embodiments u is 0; v is 1; and $Ar^4$ is phenyl.

In some embodiments u is 1; v is 1; $Ar^4$ is phenyl and Ak is $C_{1-12}$ alkylene.

Where present, substituents of $Ar^4$ may be a substituent $R^8$ wherein $R^8$ in each occurrence is independently selected from $C_{1-20}$ alkyl wherein one or more non-adjacent, non-terminal C atoms may be replaced by O, S, $NR^7$, CO or COO wherein $R^7$ is a $C_{1-12}$ hydrocarbyl and one or more H atoms of the $C_{1-20}$ alkyl may be replaced with F.

If v is 3 or more then $-(Ar^4)v$ may be a linear or branched chain of $Ar^4$ groups. A linear chain of $Ar^4$ groups as described herein has only one monovalent terminal $Ar^4$ group whereas a branched chain of $Ar^4$ groups has at least two monovalent terminal $Ar^4$ groups.

Optionally, at least one of $R^5$ and $R^6$ in each occurrence is phenyl which is unsubstituted or substituted with one or more substituents selected from $R^8$ as described above.

Optionally, $Ar^1$ and $Ar^2$ are each independently selected from thiophene, furan, bithiophene and bifuran.

Optionally, the EDG is selected from formula (IIb):

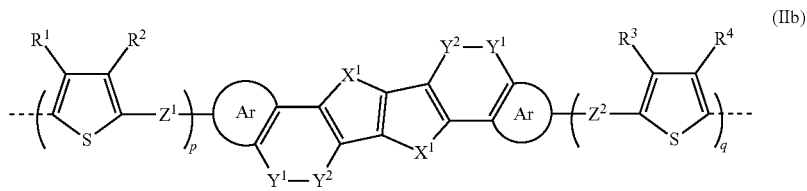

(IIb)

Optionally, each $R^1$ to $R^4$ is independently selected from:
H;
$C_{1-12}$ alkyl wherein one or more non-adjacent, non-terminal C atoms may be replaced with O, S, COO or CO; and
an aromatic or heteroaromatic group $Ar^3$ which is unsubstituted or substituted with one or more substituents.

In some embodiments, $Ar^3$ maybe an aromatic group, e.g. phenyl.

The one or more substituents of $Ar^3$, if present, may be selected from $C_{1-12}$ alkyl wherein one or more non-adjacent, non-terminal C atoms may be replaced with O, S, COO or CO.

By "non-terminal" C atom of an alkyl group as used herein is meant a C atom of the alkyl other than the methyl C atom of a linear (n-alkyl) chain or the methyl C atoms of a branched alkyl chain.

Optionally, each $R^5$ and $R^6$ is independently selected independently in each occurrence are selected from the group consisting of:
linear, branched or cyclic $C_{1-20}$ alkyl wherein one or more non-adjacent, non-terminal C atoms may be replaced by O, S, $NR^7$, CO or COO wherein $R^7$ is a $C_{1-12}$ hydrocarbyl and one or more H atoms of the $C_{1-20}$ alkyl may be replaced with F; and
a group of formula $(Ak)u-(Ar^4)v$ wherein Ak is a $C_{1-12}$ alkylene chain in which one or more C atoms may be Optionally, Ar is independently selected from thiophene, furan, bifuran and bithiophene, which may be unsubstituted or substituted with one or more substituents selected from H;
$C_{1-12}$ alkyl wherein one or more non-adjacent, non-terminal C atoms may be replaced with O, S, COO or CO; and
an aromatic or heteroaromatic group $Ar^3$ which is unsubstituted or substituted with one or more substituents.

In some embodiments, each $R^1$ to $R^4$ is H; $C_{1-20}$ alkyl; or $C_{1-20}$ alkoxy.

In some embodiments at least one of, optionally both of, $R^2$ and $R^3$ is not H, and each $R^1$ and $R^4$ is H.

Optionally, each of p and q is at least 1. Optionally, each of p and q is 1.

Optionally, at least one of p and q is 2.

Optionally, $Z^1$ is linked to $R^2$ to form a monocyclic aromatic or heteroaromatic group and/or $Z^2$ is linked to $R^3$ to form a monocyclic aromatic or heteroaromatic group.

Optionally, $Z^1$ is linked to $R^2$ to form a thiophene ring or furan ring and/or $Z^2$ is linked to $R^3$ to form a thiophene ring or furan ring.

Optionally, in the case where $Z^1$ is linked to $R^2$, compound of formula (IIa) has formula (IIc).

Optionally, in the case where $Z^2$ is linked to $R^3$, compound of formula (IIa) has formula (IIc).

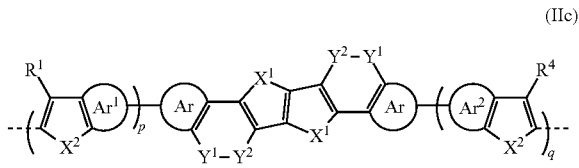

(IIc)

In some embodiments, $Ar^1$ is a monocyclic aromatic or heteroaromatic group.

In some embodiments, $Ar^2$ is a mono monocyclic aromatic or heteroaromatic group.

Each EAG has a LUMO level that is deeper (i.e. further from vacuum) than that of EDG, preferably at least 1 eV deeper. The LUMO levels of EAG and EDG may be as determined by modelling the LUMO level of EAG-H with that of H-EDG-H, i.e. by replacing the bonds between EAG and EDG with bonds to a hydrogen atom. Modelling may be performed using Gaussian09 software available from Gaussian using Gaussian09 with B3LYP (functional) and LACVP* (Basis set).

Optionally, each EAG is a group of formula (III) or (IV):

(III)

(IV)

Wherein A is a 5- or 6-membered ring which is unsubstituted or substituted with one or more substituents; $R^{10}$ and $R^{11}$ independently in each occurrence is a substituent; and $Ar^7$ is an aromatic or heteroaromatic group which is unsubstituted or substituted with one or more substituents.

Optionally, each EAG is a group of formula (V):

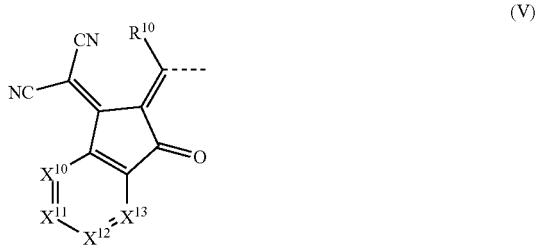

(V)

wherein:
$R^{10}$ in each occurrence is H or a substituent;
---- represents a linking position to EDG; and
each $X^{10}$ to $X^{13}$ is independently $CR^{13}$ or N wherein $R^{13}$ in each occurrence is H or a substituent.

Optionally, each $R^{13}$ is independently selected from H; $C_{1-12}$ alkyl; and an electron withdrawing group. Optionally, the electron withdrawing group is F or CN.

$R^{10}$ is preferably H.

Substituents $R^{10}$ are preferably selected from the group consisting of $C_{1-12}$ alkyl wherein one or more non-adjacent, non-terminal C atoms may be replaced with O, S, COO or CO and one or more H atoms of the alkyl may be replaced with F; and an aromatic group $Ar^9$, optionally phenyl, which is unsubstituted or substituted with one or more substituents selected from F and $C_{1-12}$ alkyl wherein one or more non-adjacent, non-terminal C atoms may be replaced with O, S, COO or CO.

Optionally, $R^1$ and/or $R^4$ is $B(R^{14})_2$ wherein $R^{14}$ in each occurrence is a substituent, optionally a $C_{1-20}$ hydrocarbyl group, and one or both EAG groups is an unsubstituted or substituted heteroaromatic group of formula (VI):

(VI)

wherein $Ar^8$ is a monocyclic or fused heteroaromatic group which is unsubstituted or substituted with one or more substituents; → is a bond to the boron atom of $R^1$ or $R^4$; and ---- is the bond to EDG.

The, or each, substituent of $Ar^8$ (if present) is independently selected from H or a substituent.

Optionally, each, substituent of $Ar^8$ is independently selected from:

H;

$C_{1-12}$ alkyl wherein one or more non-adjacent, non-terminal C atoms may be replaced with O, S, COO or CO; and an aromatic or heteroaromatic group $Ar^3$ which is unsubstituted or substituted with one or more substituents.

The one or more substituents of $Ar^3$, if present, may be selected from $C_{1-12}$ alkyl wherein one or more non-adjacent, non-terminal C atoms may be replaced with O, S, COO or CO.

By "non-terminal" C atom of an alkyl group as used herein is meant a C atom of the alkyl other than the methyl C atom of a linear (n-alkyl) chain or the methyl C atoms of a branched alkyl chain.

Optionally, $R^{14}$ is a $C_{1-20}$ hydrocarbyl group and is selected from $C_{1-12}$ alkyl; unsubstituted heteroaromatic or substituted heteroaromatic including but not limited to pyridyl;

unsubstituted phenyl; phenyl substituted with one or more $C_{1-12}$ alkyl groups or an electron withdrawing group including but not limited to halogen, including F, Br and Cl, $NO_2$ and CN.

Preferably the electron withdrawing group is F or CN.

Optionally, the group of formula (VI) is selected from formulae (VIa), (VIb) and (VIc):

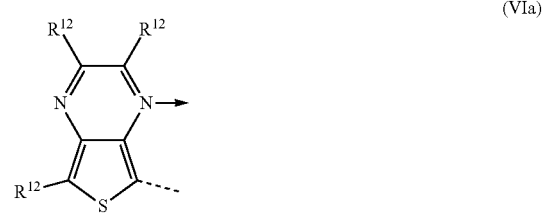

(VIa)

-continued

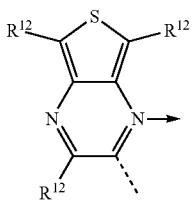
(VIb)

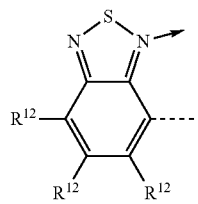
(VIc)

wherein $R^{12}$ in each occurrence is independently H or a substituent, optionally H or a substituent as described with reference to substituents of $Ar^8$.

EDG, EAG and the $B(R^{14})_2$ substituent of EDG, may be linked together to form a 5- or 6-membered ring.

U.S. Pat. No. 10,038,148 describes the synthesis of borylated compounds, the contents of which are incorporated here by reference.

Optionally, EAG is selected from formulae (XIV)-(XXV):

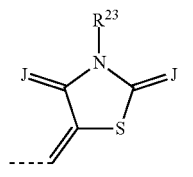
(IXVa)

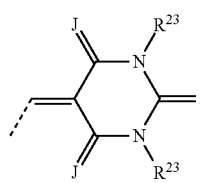
(IXVb)

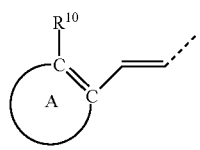
(XVa)

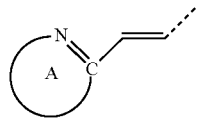
(XVb)

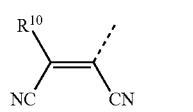
(XVIa)

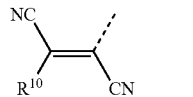
(XVIb)

-continued

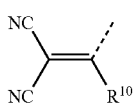
(XVIc)

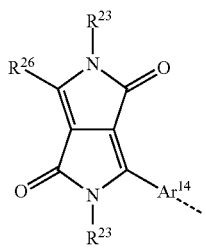
(XVII)

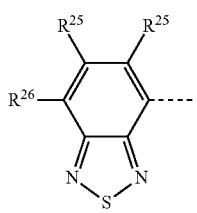
(XVIII)

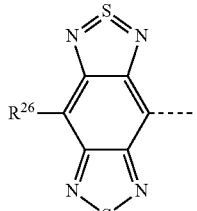
(XIX)

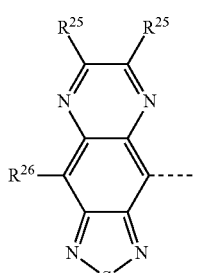
(XX)

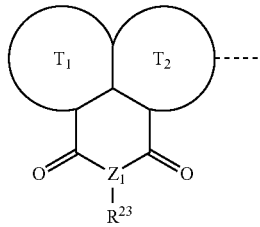
(XXI)

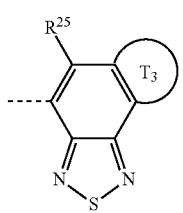
(XXII)

-continued

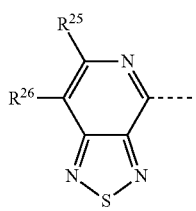
(XXIV)

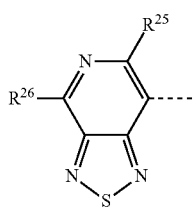
(XXV)

J is O or S.

A is a 5- or 6-membered ring which is unsubstituted or substituted with one or more substituents and which may be fused to one or more further rings.

$R^{23}$ in each occurrence is a substituent, optionally $C_{1-12}$ alkyl wherein one or more non-adjacent, non-terminal C atoms may be replaced with O, S, COO or CO and one or more H atoms of the alkyl may be replaced with F.

$R^{25}$ in each occurrence is independently H; F; $C_{1-12}$ alkyl wherein one or more non-adjacent, non-terminal C atoms may be replaced with O, S, COO or CO and one or more H atoms of the alkyl may be replaced with F; or an aromatic group $Ar^2$, optionally phenyl, which is unsubstituted or substituted with one or more substituents selected from F and $C_{1-12}$ alkyl wherein one or more non-adjacent, non-terminal C atoms may be replaced with O, S, COO or CO.

$R^{26}$ is a substituent, preferably a substituent selected from:

—$(Ar^{13})w$ wherein $Ar^{13}$ in each occurrence is independently an unsubstituted or substituted aryl or heteroaryl group, preferably thiophene, and w is 1, 2 or 3;

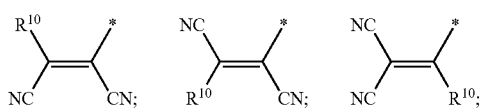

and $C_{1-12}$ alkyl wherein one or more non-adjacent, non-terminal C atoms may be replaced with O, S, COO or CO and one or more H atoms of the alkyl may be replaced with F.

$Ar^{14}$ is a 5-membered heteroaromatic group, preferably thiophene or furan, which is unsubstituted or substituted with one or more substituents.

Substituents of $Ar^{13}$ and $Ar^{14}$, where present, are optionally selected from $C_{1-12}$ alkyl wherein one or more non-adjacent, non-terminal C atoms may be replaced with O, S, COO or CO and one or more H atoms of the alkyl may be replaced with F.

$Z^1$ is N or P.

$T^1$, $T^2$ and $T^3$ each independently represent an aryl or a heteroaryl ring which may be fused to one or more further rings. Substituents of $T^1$, $T^2$ and $T^3$, where present, are optionally selected from non-H groups of $R^{12}$.

Exemplary groups of formula (XIVa) or (XIVb) include:

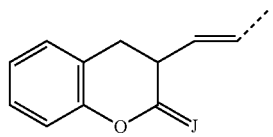

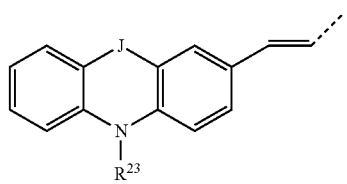

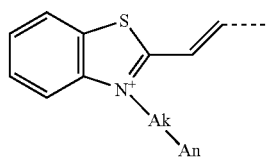

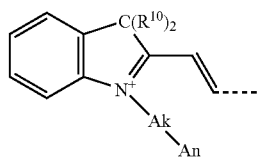

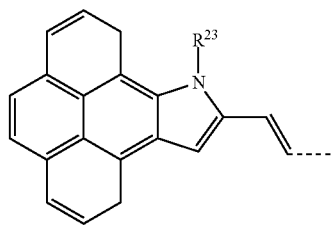

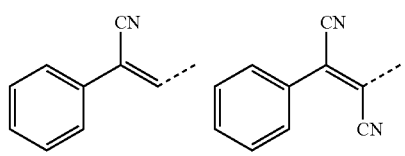

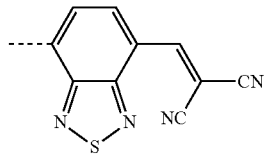

wherein Ak is a $C_{1-12}$ alkylene chain in which one or more C atoms may be replaced with O, S, CO or COO; An is an anion, optionally —$SO_3^-$; and each benzene ring is independently unsubstituted or substituted with one or more substituents selected from substituents described with reference to $R^{10}$.

Exemplary EAGs of formula (XXI) are:
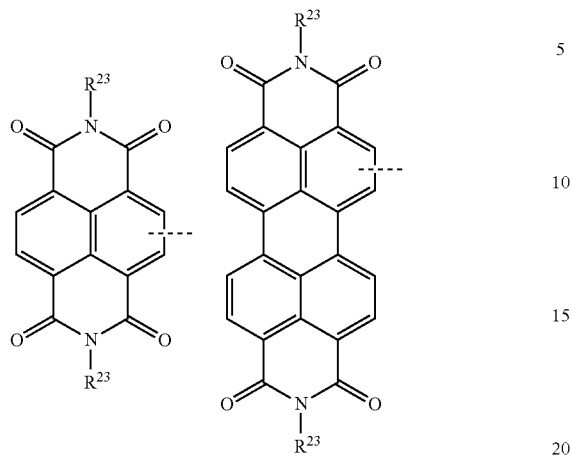
Optionally, the compound of formula (I) has formula (VII):
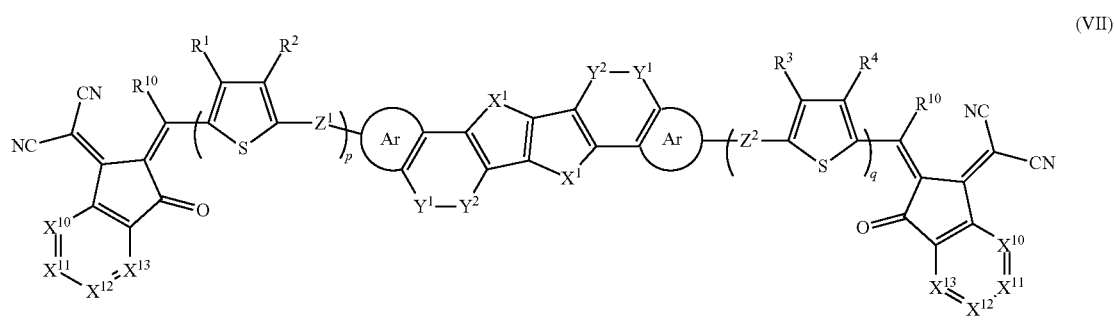
Optionally Ar is substituted with one or more substituent wherein the substituent is selected from the group defined previously for $R^5$ and $R^6$.
Exemplary compounds of formula (I) are:
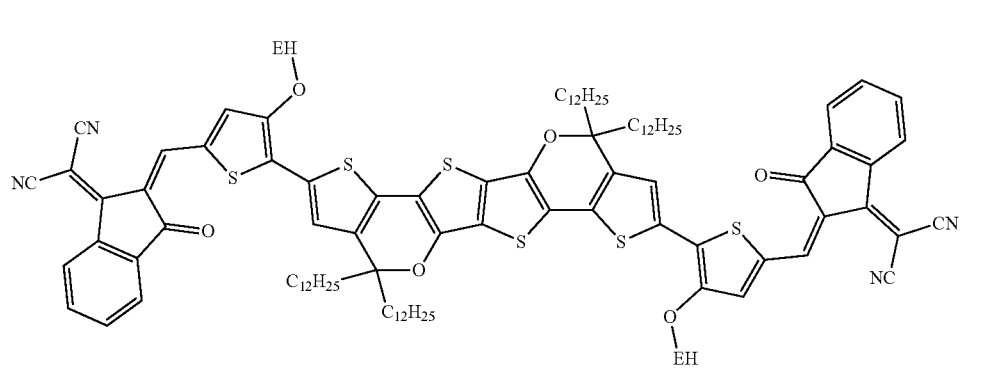

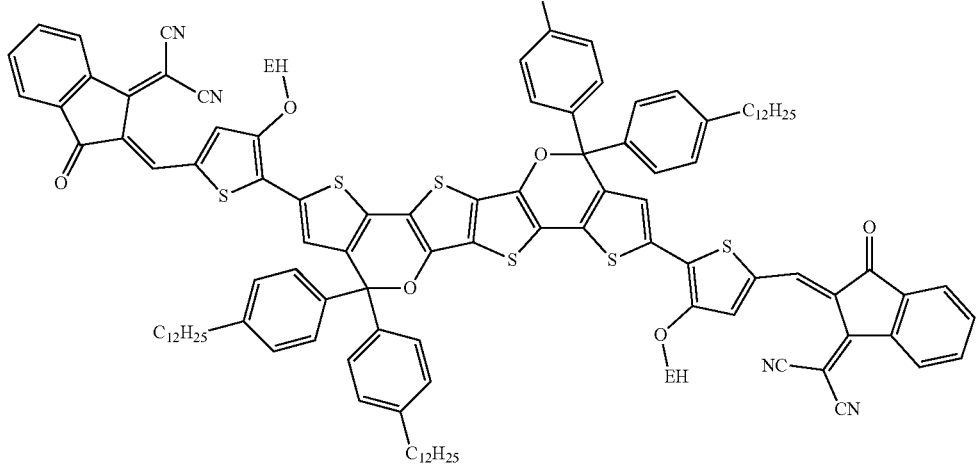
(2)
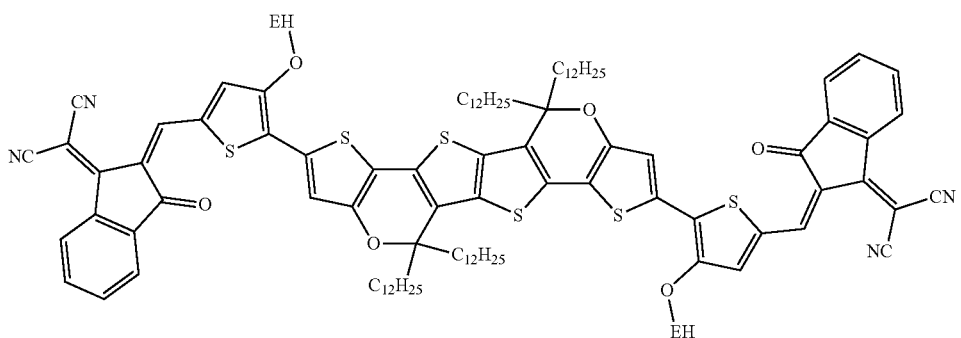
(3)
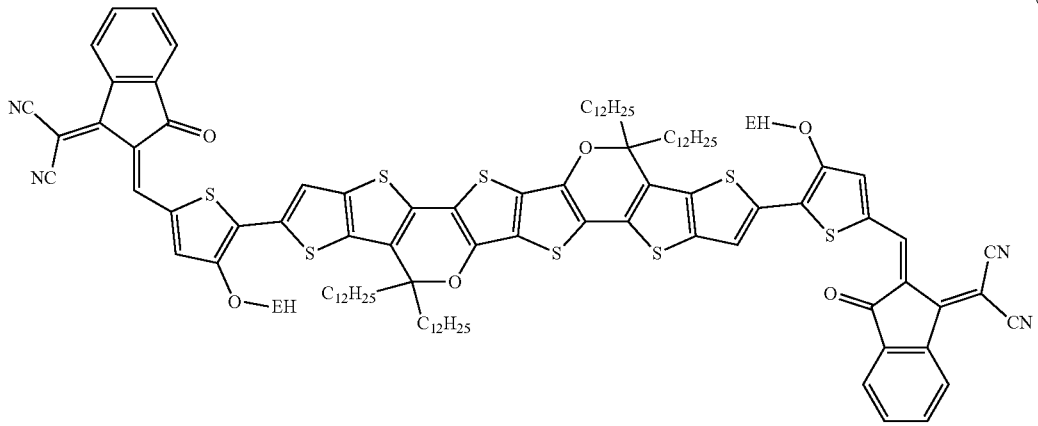
(4)

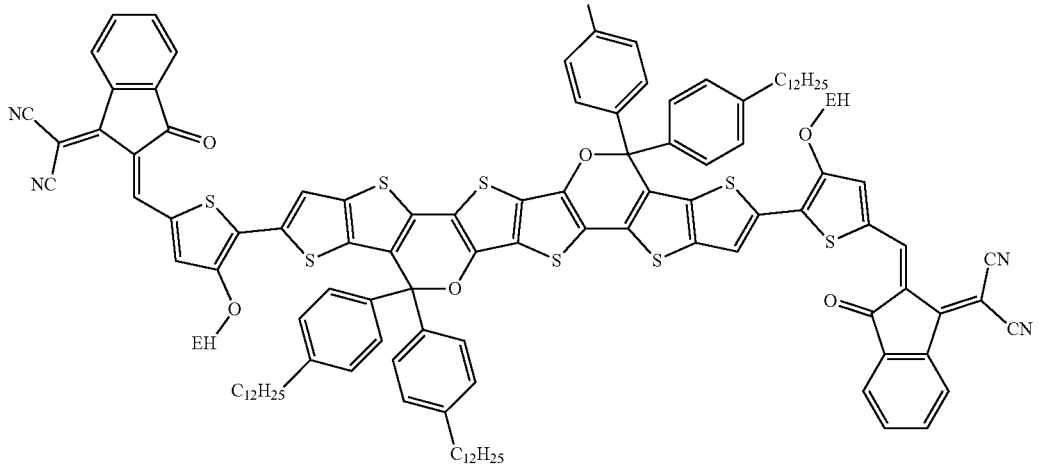
(5)
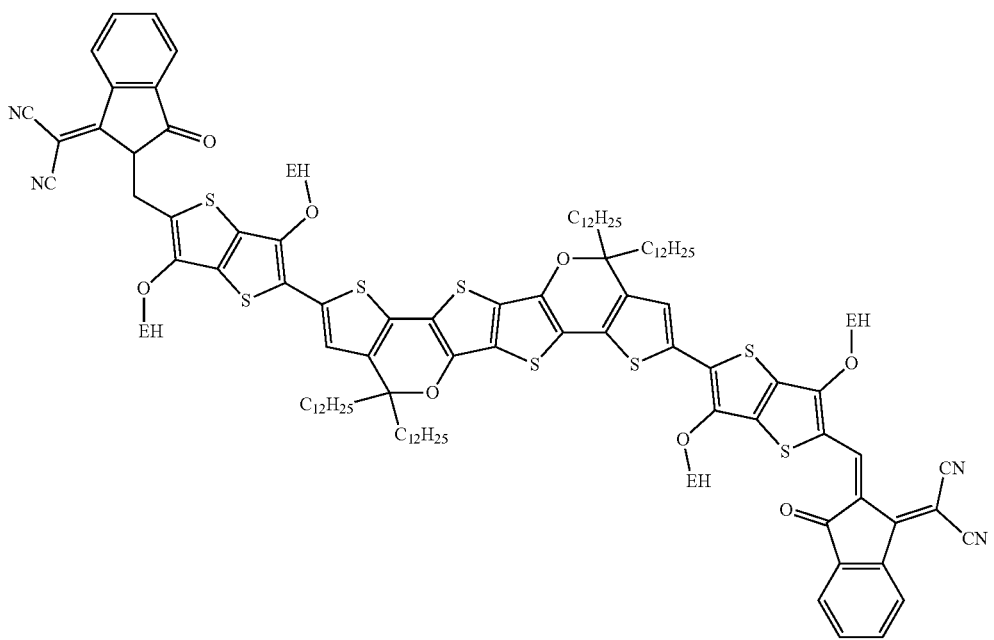
(6)
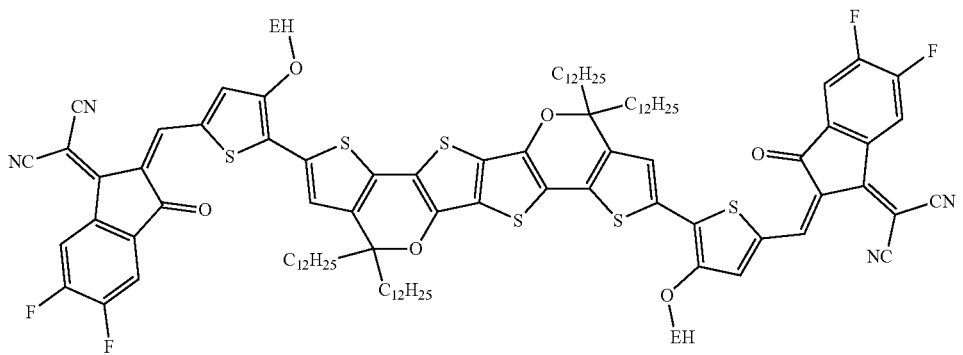
(7)

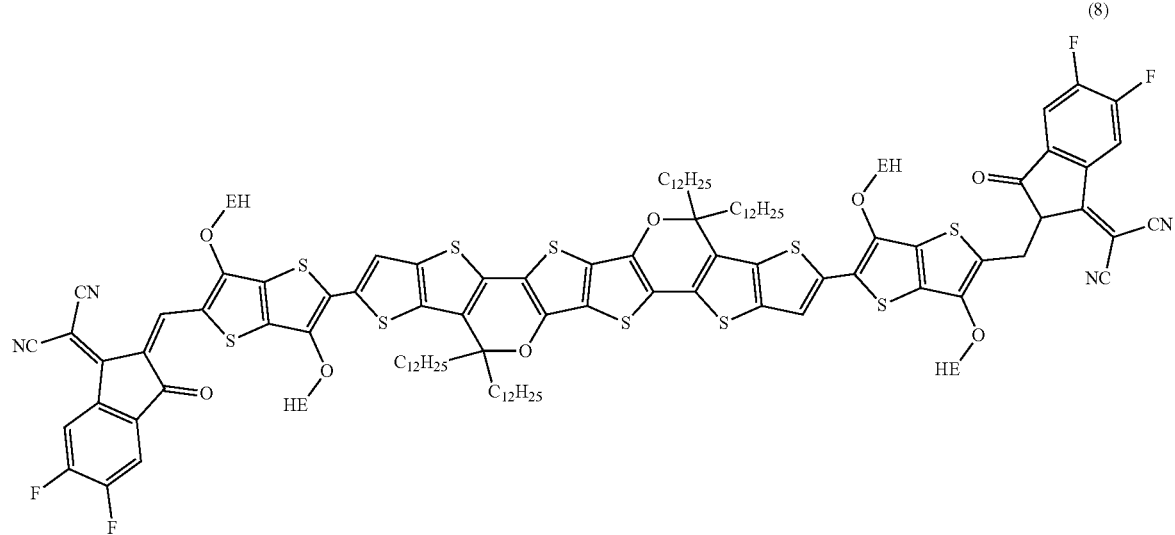
(8)
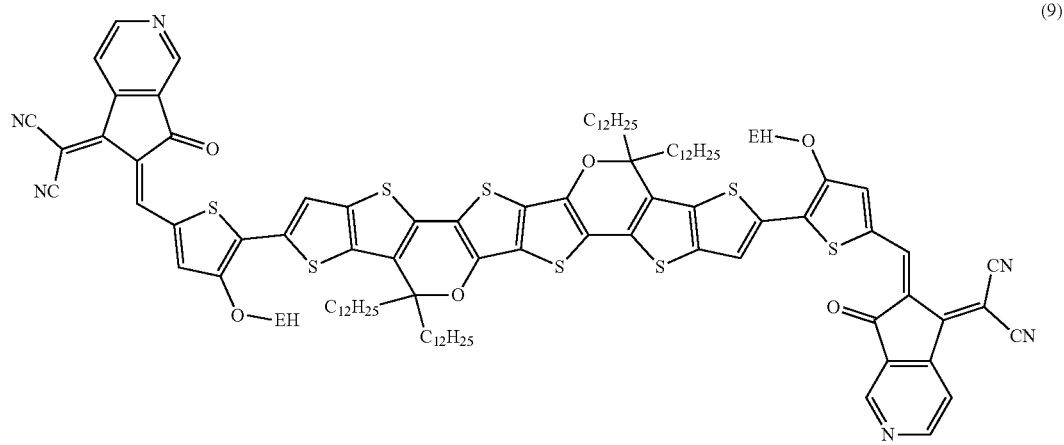
(9)
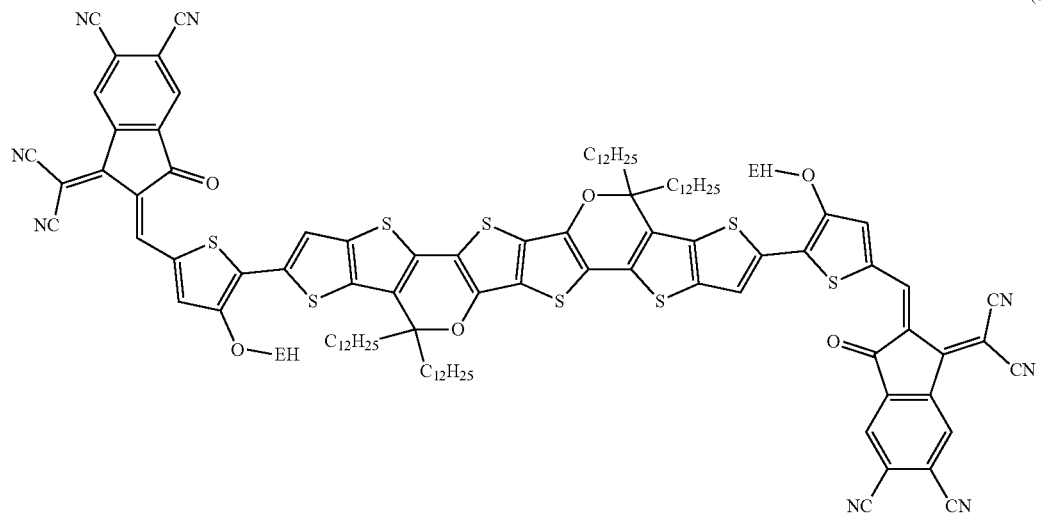
(10)

-continued
(11)
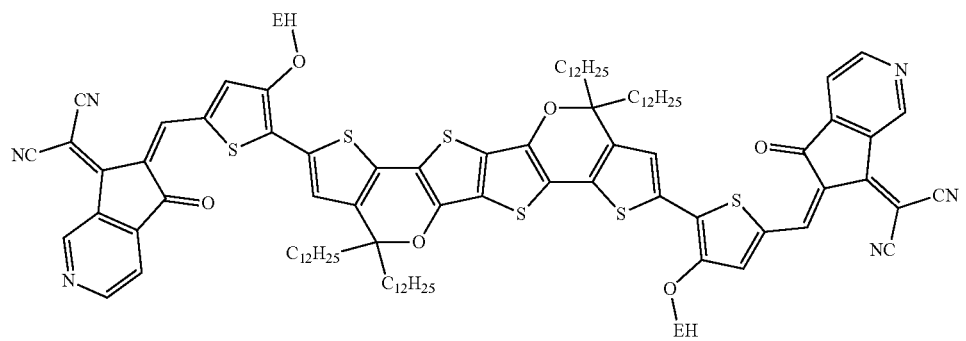
(12)
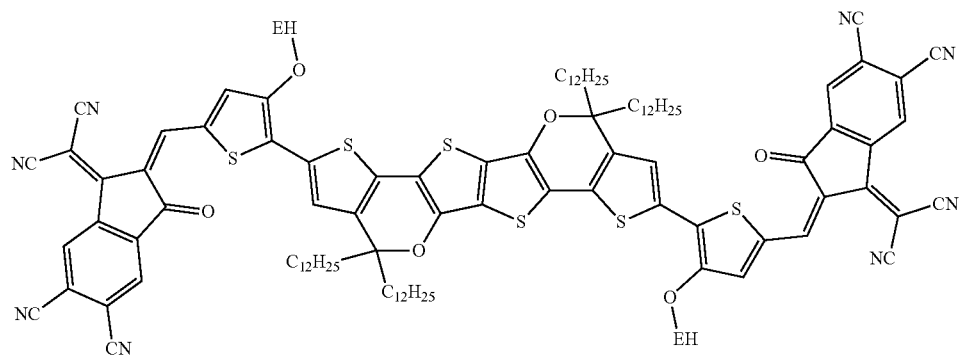
(13)
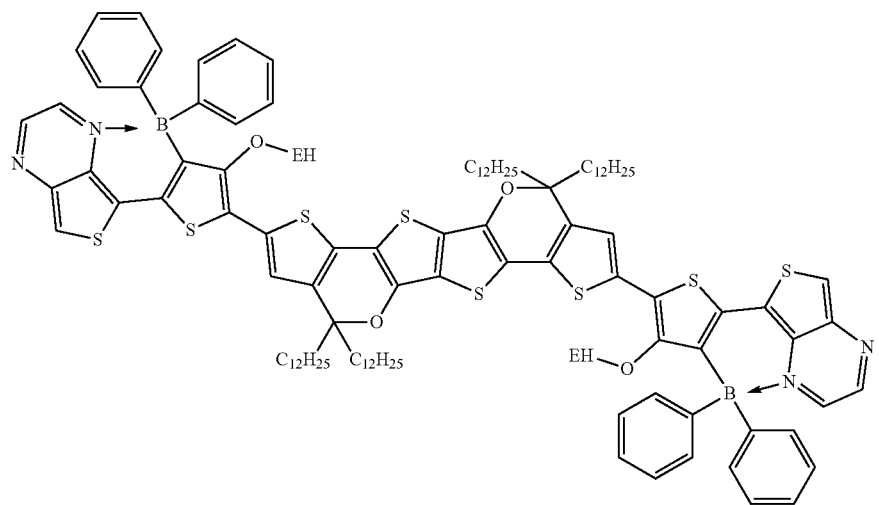

(14)
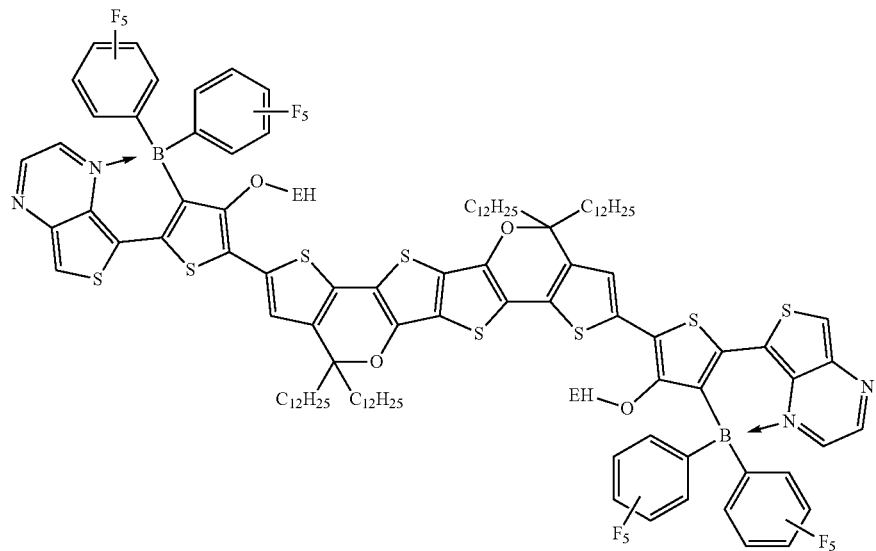
(15)
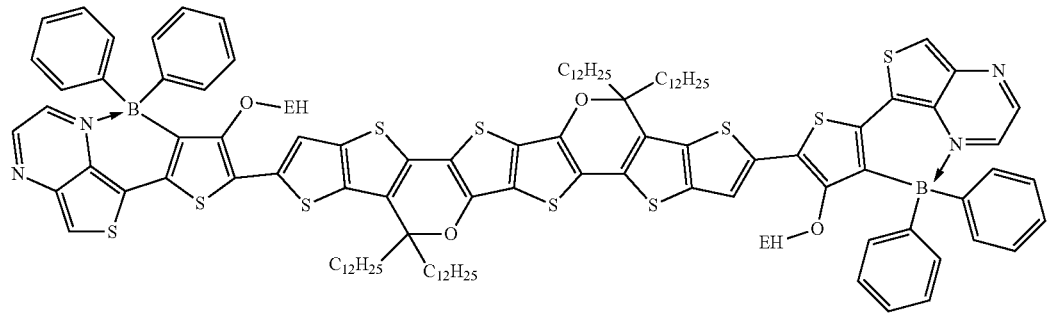
(16)
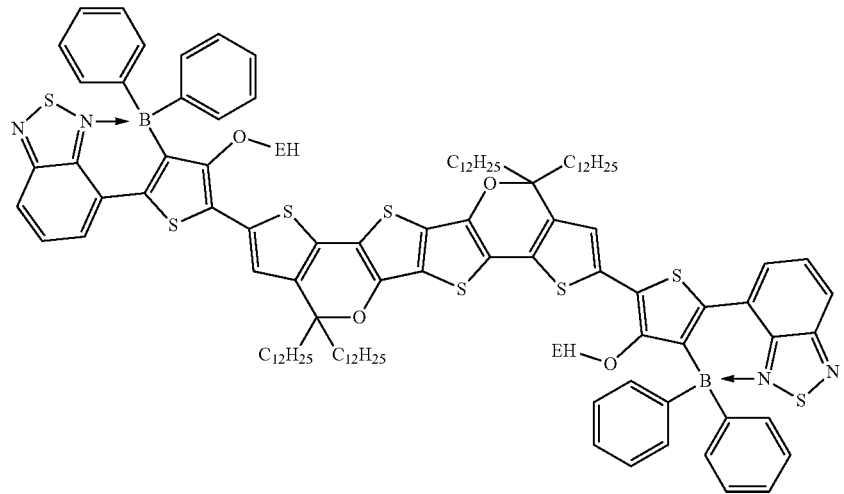

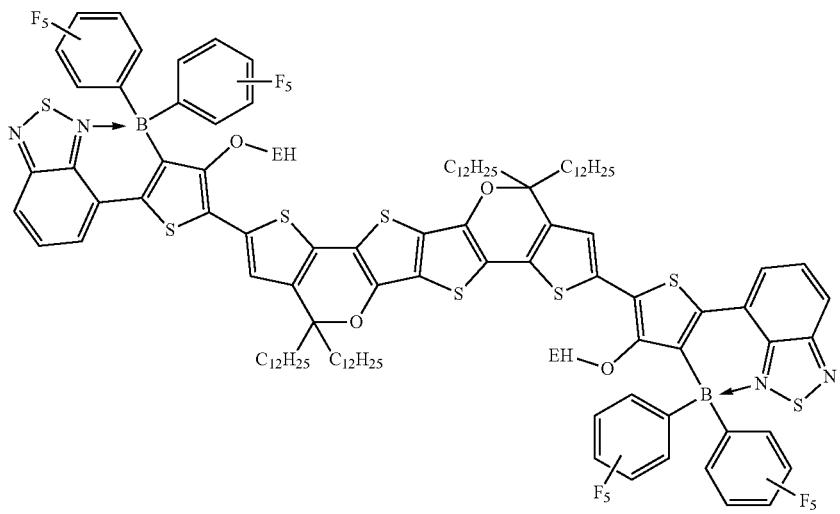
(17)
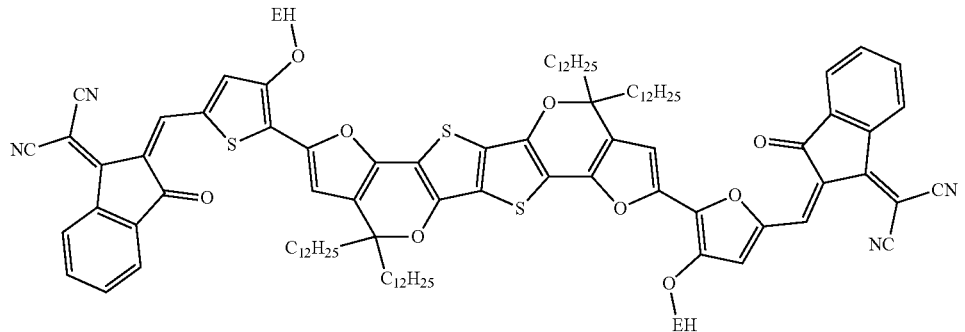
(18)
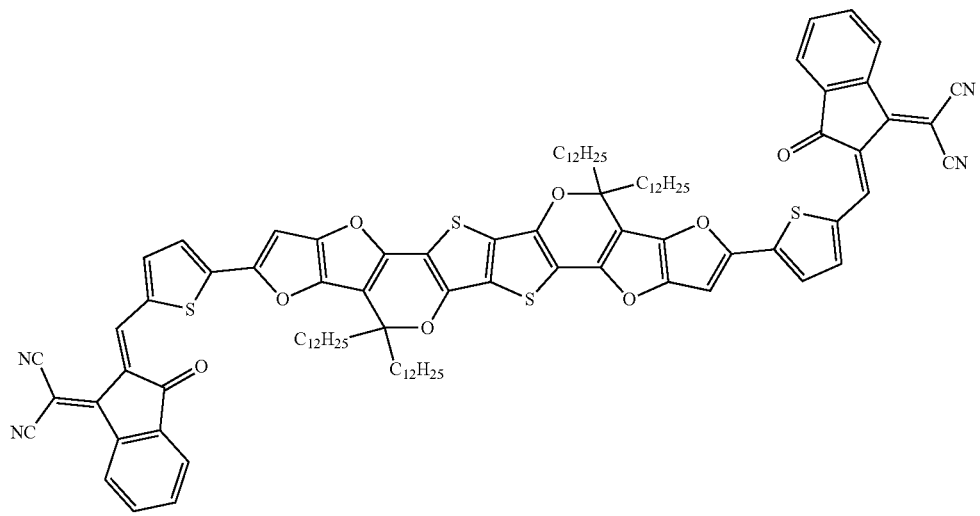
(19)

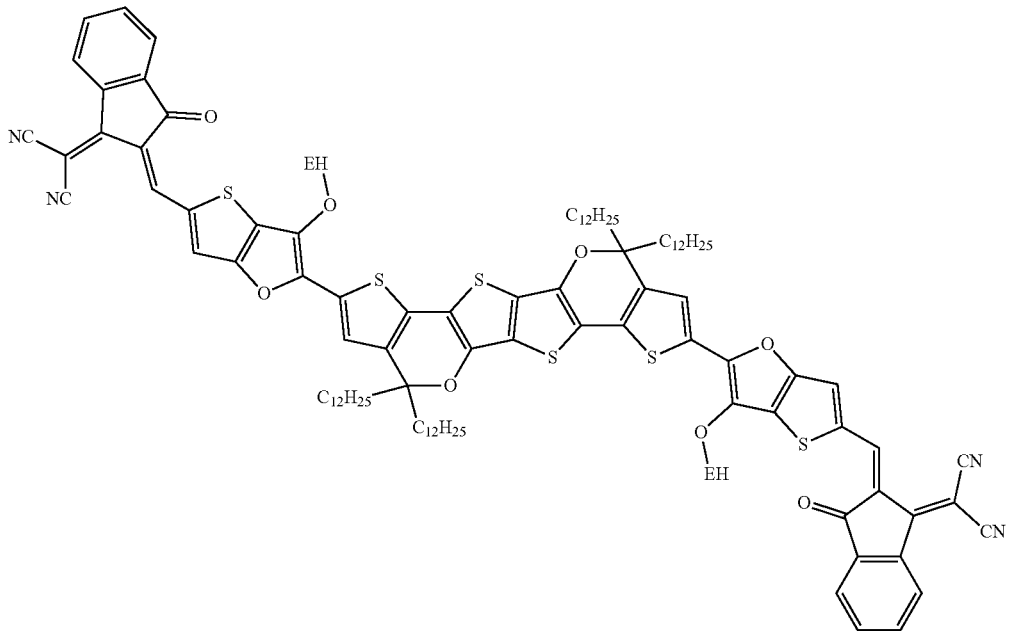

(20)

wherein EH is ethylhexyl.

The compound of formula (I) may be used in combination with a fullerene acceptor.

The compound of formula (I): fullerene acceptor weight ratio may be in the range of about 1:0.1-1:1, preferably in the range of about 1:0.1-1:0.5.

The fullerene may be a $C_{60}$, $C_{70}$, $C_{76}$, $C_{78}$ or $C_{84}$ fullerene or a derivative thereof including, without limitation, PCBM-type fullerene derivatives (including phenyl-C61-butyric acid methyl ester ($C_{60}$PCBM) and phenyl-C71-butyric acid methyl ester ($C_{70}$PCBM)), TCBM-type fullerene derivatives (e.g. tolyl-C61-butyric acid methyl ester ($C_{60}$TCBM)), and ThCBM-type fullerene derivatives (e.g. thienyl-C61-butyric acid methyl ester ($C_{60}$ThCBM)

Where present, a fullerene acceptor may have formula (VIII):

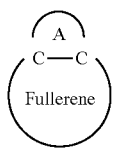

(VIII)

wherein A, together with the C—C group of the fullerene, forms a monocyclic or fused ring group which may be unsubstituted or substituted with one or more substituents.

Exemplary fullerene derivatives include formulae (IIIa), (IIIb) and (IIIc):

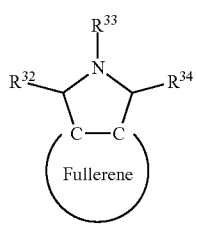

(VIIIa)

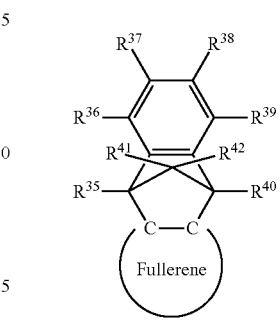

(VIIIb)

-continued

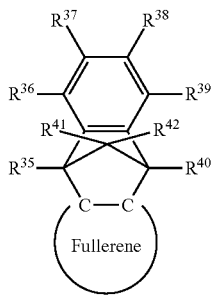

(VIIIc)

wherein $R^{30}$-$R^{42}$ are each independently H or a substituent.

Substituents $R^{30}$-$R^{42}$ are optionally and independently in each occurrence selected from the group consisting of aryl or heteroaryl, optionally phenyl, which may be unsubstituted or substituted with one or more substituents; and $C_{1-20}$ alkyl wherein one or more non-adjacent, non-terminal C atoms may be replaced with O, S, CO or COO and one or more H atoms may be replaced with F.

Substituents of aryl or heteroaryl groups $R^{30}$-$R^{42}$, where present, are optionally selected from $C_{1-12}$ alkyl wherein one or more non-adjacent, non-terminal C atoms may be replaced with O, S, CO or COO and one or more H atoms may be replaced with F.

In some embodiments the electron acceptor compound of formula (I) forms a composition comprising a compound of formula (I) and an electron-donating material capable of donating an electron to the compound.

The donor (p-type) compound is not particularly limited and may be appropriately selected from electron donating materials that are known to the person skilled in the art, including organic polymers and non-polymeric organic molecules. The p-type compound has a HOMO deeper (further from vacuum) than a LUMO of the compound of formula (I). Optionally, the gap between the HOMO level of the p-type donor and the LUMO level of the n-type acceptor compound of formula (I) is less than 1.4 eV.

In a preferred embodiment the p-type donor compound is an organic conjugated polymer, which can be a homopolymer or copolymer including alternating, random or block copolymers. Preferred are non-crystalline or semi-crystalline conjugated organic polymers. Further preferably the p-type organic semiconductor is a conjugated organic polymer with a low bandgap, typically between 2.5 eV and 1.5 eV, preferably between 2.3 eV and 1.8 eV.

Optionally, the p-type donor has a HOMO level no more than 5.5 eV from vacuum level. Optionally, the p-type donor has a HOMO level at least 4.1 eV from vacuum level.

As exemplary p-type donor polymers, polymers selected from conjugated hydrocarbon or heterocyclic polymers including polyacene, polyaniline, polyazulene, polybenzofuran, polyfluorene, polyfuran, polyindenofluorene, polyindole, polyphenylene, polypyrazoline, polypyrene, polypyridazine, polypyridine, polytriarylamine, poly(phenylene vinylene), poly(3-substituted thiophene), poly(3,4-bisubstituted thiophene), polyselenophene, poly(3-substituted selenophene), poly(3,4-bisubstituted selenophene), poly(bisthiophene), poly(terthiophene), poly(bisselenophene), poly(terselenophene), polythieno[2,3-b]thiophene, polythieno[3,2-b]thiophene, polybenzothiophene, polybenzo[1,2-b:4,5-b']dithiophene, polyisothianaphthene, poly(monosubstituted pyrrole), poly(3,4-bisubstituted pyrrole), poly-1,3,4-oxadiazoles, polyisothianaphthene, derivatives and co-polymers thereof may be mentioned. Preferred examples of p-type donors are copolymers of polyfluorenes and polythiophenes, each of which may be substituted, and polymers comprising benzothiadiazole-based and thiophene-based repeating units, each of which may be substituted. It is understood that the p-type donor may also consist of a mixture of a plurality of electron donating materials.

Optionally, the donor polymer comprises a repeat unit of formula (XXX):

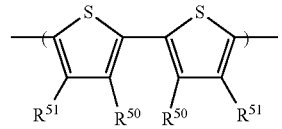

(XXX)

wherein $R^{50}$ and $R^{51}$ independently in each occurrence is H or a substituent.

Substituents $R^{50}$ and $R^{51}$ may be selected from groups other than H described with respect to $R^1$-$R^4$.

Preferably, each $R^{50}$ is a substituent. In a preferred embodiment, the $R^{50}$ groups are linked to form a group of formula —$Y^1$—$C(R^{52})_2$— wherein $Y^1$ is O, $NR^{53}$, or $C(R^{52})_2$; $R^{52}$ in each occurrence is H or a substituent, preferably a substituent as described with reference to $R^5$ and $R^6$, most preferably a $C_{1-30}$ hydrocarbyl group; and $R^{53}$ is a substituent, preferably a $C_{1-30}$ hydrocarbyl group.

Preferably, each $R^{51}$ is H.

Optionally, the donor polymer comprises a repeat unit selected from repeat units of formulae:

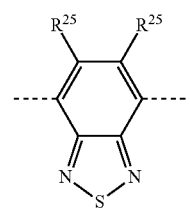

(XVIIIa)

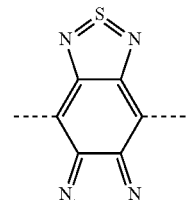

(XIXa)

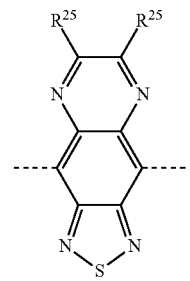

(XXa)

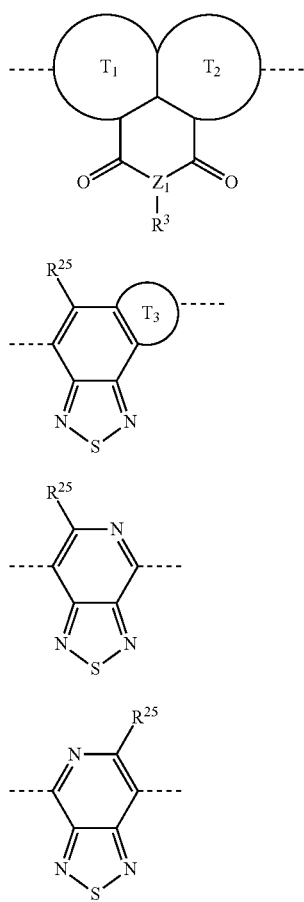

(XXIa)

(XXIIa)

(XXIVa)

(XXVa)

wherein $R^{25}$, $Z^1$, $R^{23}$ and $R^{25}$ are as described above.

Exemplary donor materials are disclosed in, for example, WO2013/051676, the contents of which are incorporated herein by reference.

Optionally, the p-type donor has a HOMO level no more than 5.5 eV from vacuum level.

Optionally, the p-type donor has a HOMO level at least 4.1 eV from vacuum level.

In some embodiments, the weight of the donor compound to the acceptor compound is from about 1:0.5 to about 1:2.

Preferably, the weight ratio of the donor compound to the acceptor compound is about 1:1 or about 1:1.5.

At least one of the first and second electrodes is transparent so that light incident on the device may reach the bulk heterojunction layer. In some embodiments, both of the first and second electrodes are transparent.

Each transparent electrode preferably has a transmittance of at least 70%, optionally at least 80%, to wavelengths in the range of 300-900 nm.

In some embodiments, one electrode is transparent and the other electrode is reflective.

Optionally, the transparent electrode comprises or consists of a layer of transparent conducting oxide, preferably indium tin oxide or indium zinc oxide. In preferred embodiments, the electrode may comprise poly 3,4-ethylenedioxythiophene (PEDOT). In other preferred embodiments, the electrode may comprise a mixture of PEDOT and polystyrene sulfonate (PSS). The electrode may consist of a layer of PEDOT:PSS.

Optionally, the reflective electrode may comprise a layer of a reflective metal. The layer of reflective material may be aluminium or silver or gold. In some embodiments, a bi-layer electrode may be used. For example, the electrode may be an indium tin oxide (ITO)/silver bi-layer, an ITO/aluminium bi-layer or an ITO/gold bi-layer.

The OPD may be formed by forming the photosensitive organic layer between one of the anode and cathode supported by a substrate and depositing the other of the anode or cathode over the photosensitive organic layer.

The area of the OPD may be less than about 3 $cm^2$, less than about 2 $cm^2$, less than about 1 $cm^2$, less than about 0.75 $cm^2$, less than about 0.5 $cm^2$ or less than about 0.25 $cm^2$. The substrate may be, without limitation, a glass or plastic substrate. The substrate can be described as an inorganic semiconductor. In some embodiments, the substrate may be silicon. For example, the substrate can be a wafer of silicon. The substrate is transparent if, in use, incident light is to be transmitted through the substrate and the electrode supported by the substrate.

The substrate supporting one of the anode and cathode may or may not be transparent if, in use, incident light is to be transmitted through the other of the anode and cathode.

The bulk heterojunction layer may be formed by any process including, without limitation, thermal evaporation and solution deposition methods.

Preferably, the bulk heterojunction layer is formed by depositing a formulation comprising the acceptor material and the electron donor material dissolved or dispersed in a solvent or a mixture of two or more solvents. The formulation may be deposited by any coating or printing method including, without limitation, spin-coating, dip-coating, roll-coating, spray coating, doctor blade coating, wire bar coating, slit coating, ink jet printing, screen printing, gravure printing and flexographic printing.

The one or more solvents of the formulation may optionally comprise or consist of benzene substituted with one or more substituents selected from chlorine, $C_{1-10}$ alkyl and $C_{1-10}$ alkoxy wherein two or more substituents may be linked to form a ring which may be unsubstituted or substituted with one or more $C_{1-6}$ alkyl groups, optionally toluene, xylenes, trimethylbenzenes, tetramethylbenzenes, anisole, indane and its alkyl-substituted derivatives, and tetralin and its alkyl-substituted derivatives.

The formulation may comprise a mixture of two or more solvents, preferably a mixture comprising at least one benzene substituted with one or more substituents as described above and one or more further solvents. The one or more further solvents may be selected from esters, optionally alkyl or aryl esters of alkyl or aryl carboxylic acids, optionally a $C_{1-10}$ alkyl benzoate, benzyl benzoate or dimethoxybenzene. In preferred embodiments, a mixture of trimethylbenzene and benzyl benzoate is used as the solvent. In other preferred embodiments, a mixture of trimethylbenzene and dimethoxybenzene is used as the solvent.

The formulation may comprise further components in addition to the electron acceptor, the electron donor and the one or more solvents. As examples of such components, adhesive agents, defoaming agents, deaerators, viscosity enhancers, diluents, auxiliaries, flow improvers colourants, dyes or pigments, sensitizers, stabilizers, nanoparticles, surface-active compounds, lubricating agents, wetting agents, dispersing agents and inhibitors may be mentioned.

The photosensor layer comprises a bulk heterojunction layer comprising an acceptor material and the electron donor material.

In some embodiments there is provided a method of forming an OPD comprising formation of the photosensitive organic layer between one of the anode and cathode and formation of the other of the anode and cathode over the photosensitive organic layer.

In some embodiments there is provided a method wherein formation of the photosensitive organic layer comprises deposition of a formulation or a composition comprising a compound of formula (I) and an electron donating-material dissolved or dispersed in one or more solvents.

In some embodiments there is provided a method wherein the formation of the photosensitive organic layer comprises evaporation of one or more solvents.

In some embodiments, the compounds and compositions of formula (I) maybe suitable for use in other electronic devices including but not limited to organic thin film transistors, organic field effect transistors, organic light emitting diodes and organic photovoltaic cells.

The OPD as described herein may be used in a wide range of applications including, without limitation, detecting the presence and/or brightness of ambient light and in a sensor comprising the organic photodetector and a light source. The photodetector may be configured such that light emitted from the light source is incident on the photodetector and changes in wavelength and/or brightness of the light may be detected, e.g. due to absorption by and/or emission of light from a target material in a sample disposed in a light path between the light source and the organic photodetector. The sensor may be, without limitation, a gas sensor, a biosensor, an X-ray imaging device, an image sensor such as a camera image sensor, a motion sensor (for example for use in security applications) a proximity sensor or a fingerprint sensor.

In some embodiments there is provided a photosensor comprising a light source and an OPD wherein the photosensor is configured to detect light emitted from the light source, wherein the light source emits light having a peak wavelength greater than 750 nm, optionally in the range of greater than 750 nm up to 1500 nm.

In some embodiments the photosensor can be used in a method for determining the presence and/or concentration of a target material in a sample, the method comprising illuminating the sample and measuring a response of a photodetector is configured to detect light emitted from the sample upon illumination, wherein the sample is in light path between the OPD and light source.

A 1D or 2D photosensor array may comprise a plurality of photodetectors as described herein in an image sensor. The photodetector may be configured to detect light emitted from a target analyte which emits light upon irradiation by the light source or which is bound to a luminescent tag which emits light upon irradiation by the light source. The photodetector may be configured to detect a wavelength of light emitted by the target analyte or a luminescent tag bound thereto.

EXAMPLES

Synthesis

A compound of example (1) may be prepared according to the following reaction scheme:

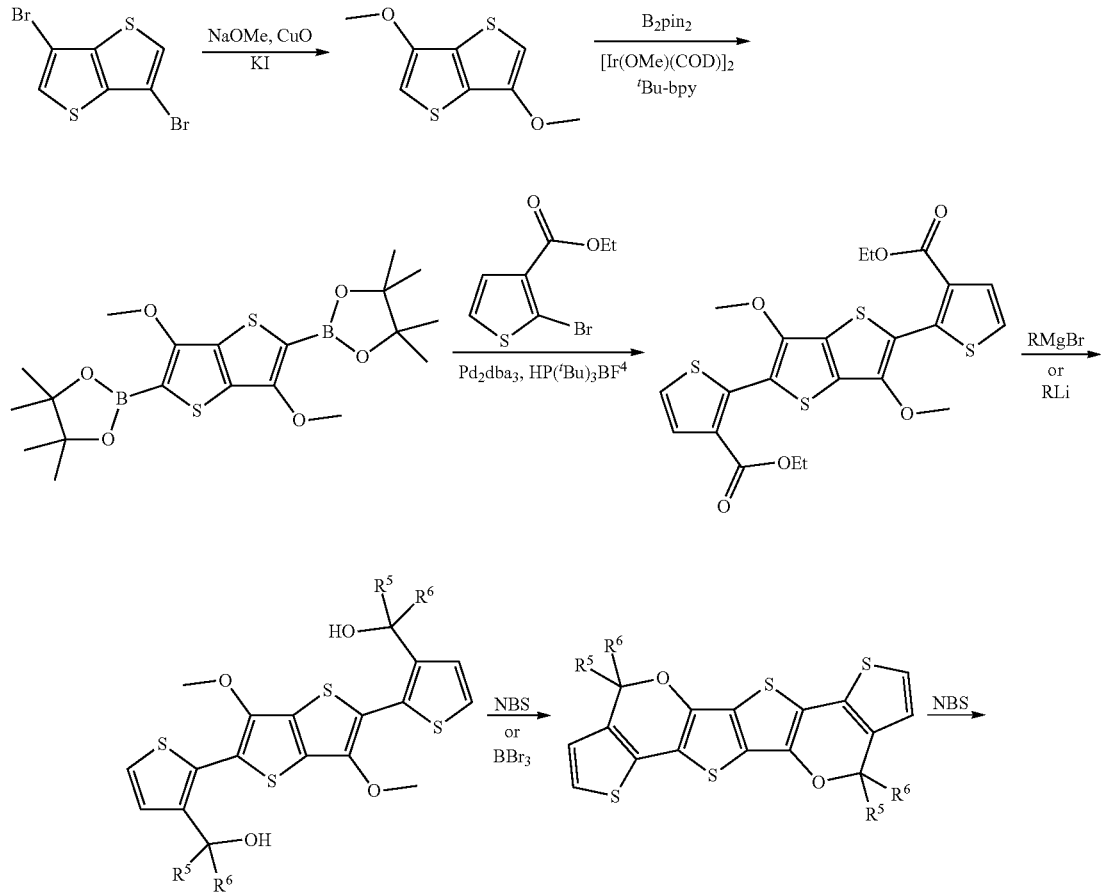

-continued
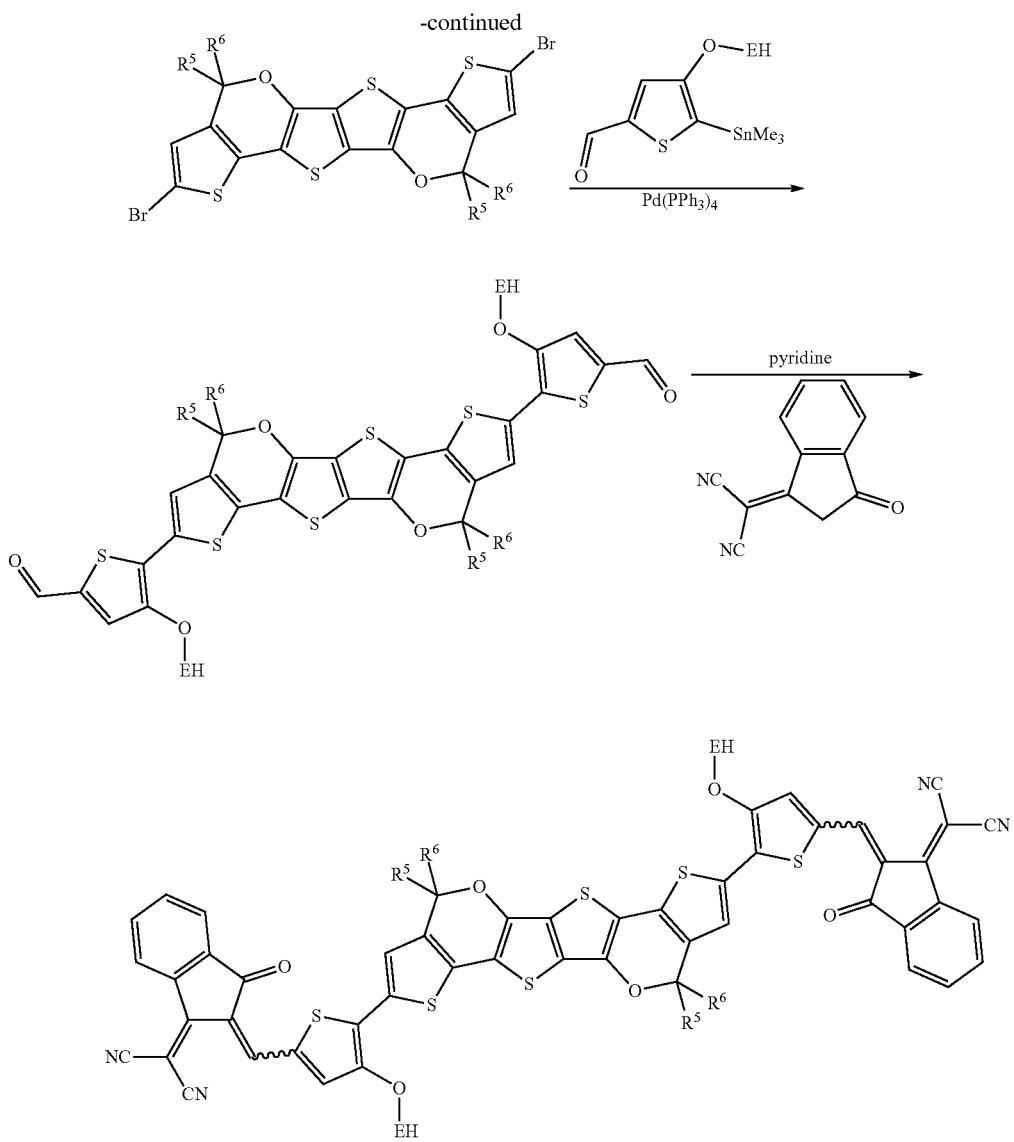
wherein each $R^5$ and $R^6$ is independently an alkyl or aryl group as described herein and EH is ethylhexyl.
Modelling Data
LUMO levels and HOMO-LUMO bandgaps of the following compounds were modelled, in which all alkyl groups were limited to methyl to simplify calculation:
Compound Example 1
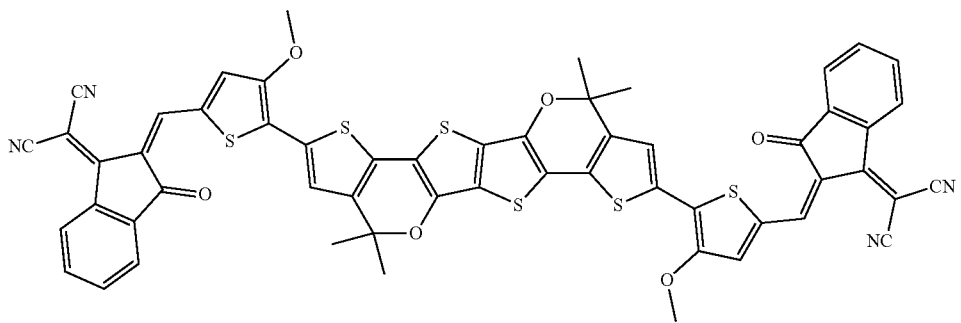

-continued
Compound Example 2
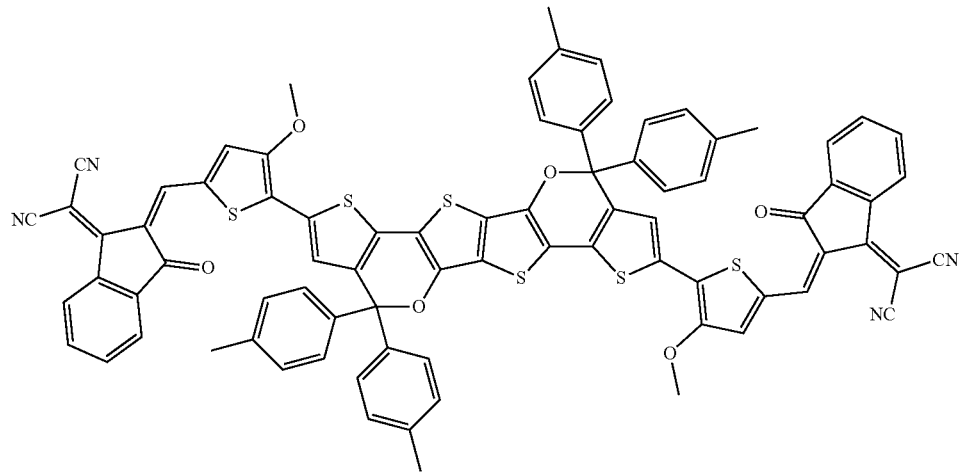
Compound Example 3
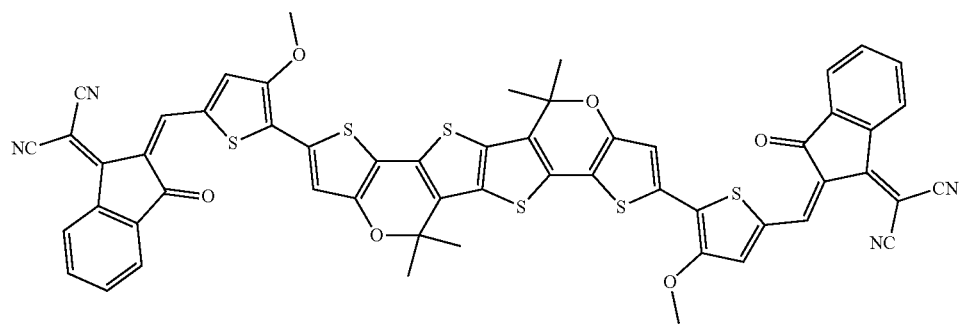
Compound Example 4
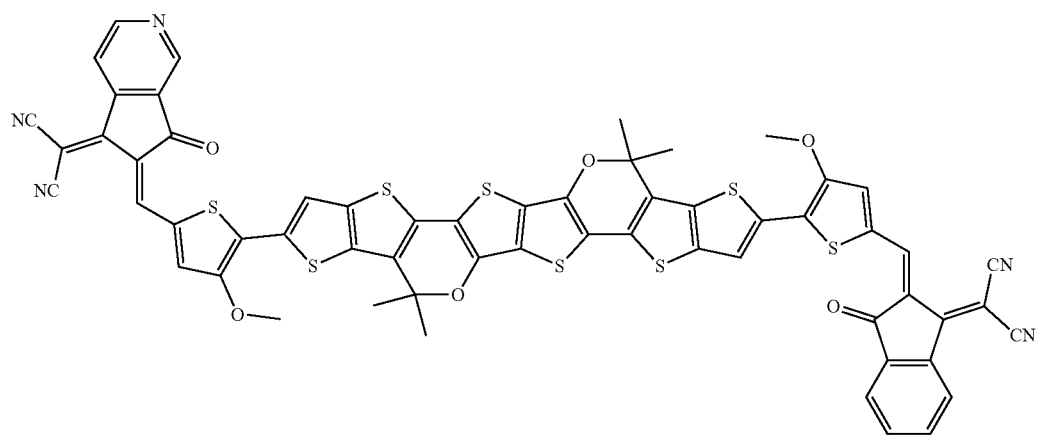

-continued
Compound Example 5
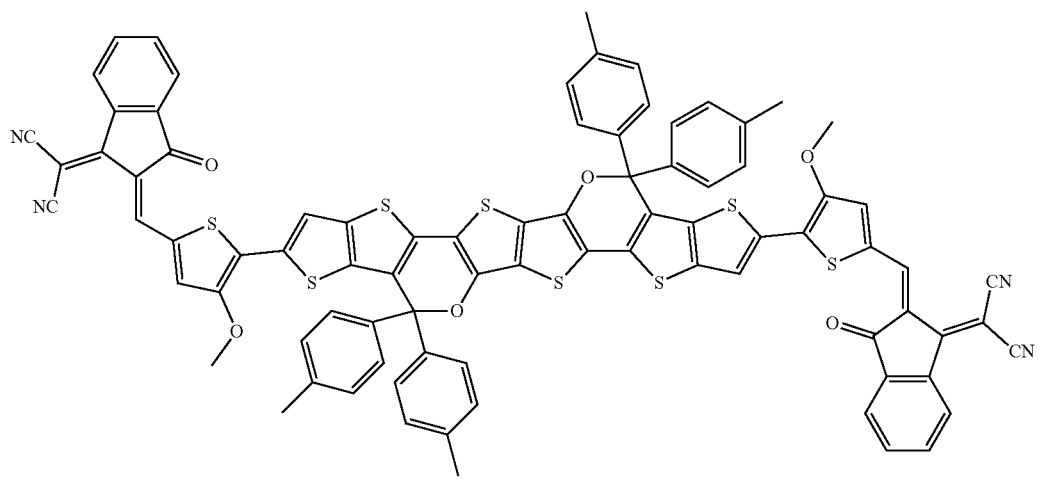
Comparative Example 1
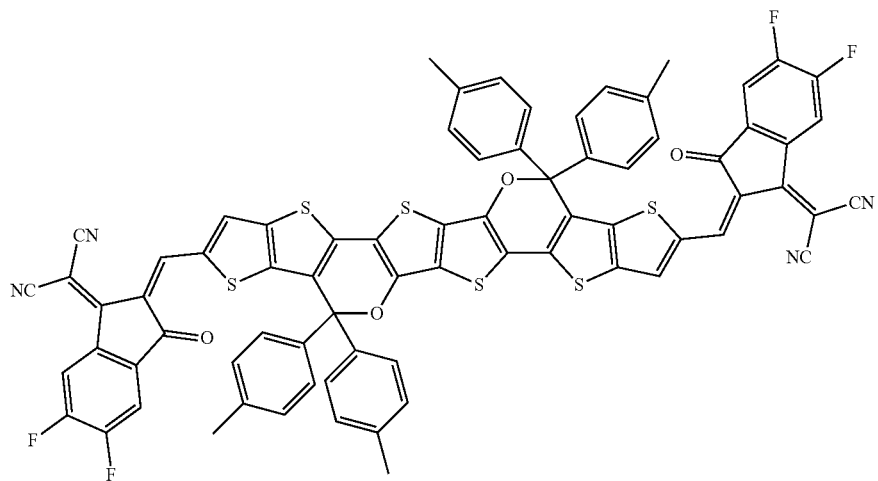
Comparative Example 2
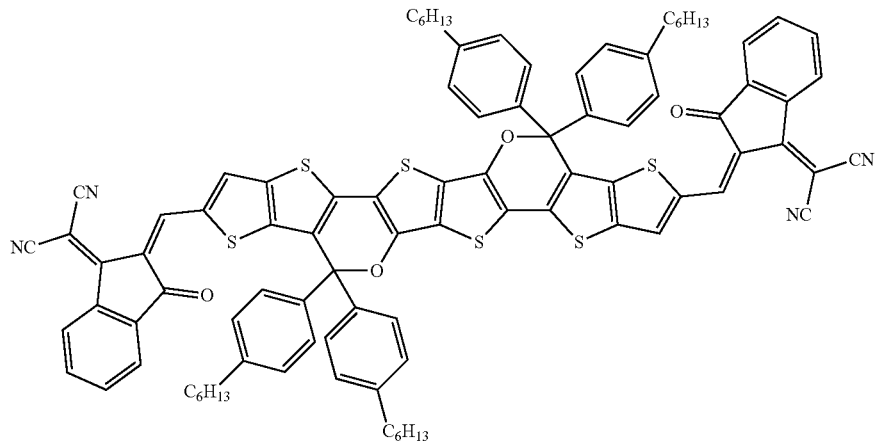

-continued

Comparative Example 3

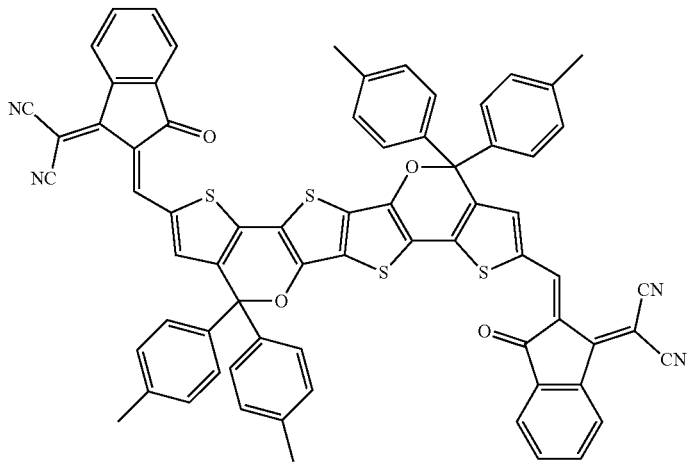

Quantum chemical modelling was performed using Gaussian09 software available from Gaussian using Gaussian09 with B3LYP (functional) and LACVP* (Basis set). For purposes of the modelling, all alkyl chains were reduced to methyl groups.

TABLE 1

| COMPOUND | HOMO (eV) | LUMO (eV) | BAND GAP (eV) |
|---|---|---|---|
| Comparative Example 1 | −5.366 | −3.501 | 1.865 |
| Comparative Example 2 | −5.241 | −3.351 | 1.890 |
| Comparative Example 3 | −5.302 | −3.375 | 1.927 |
| Compound Example 1 | −4.912 | −3.32 | 1.592 |
| Compound Example 2 | −4.871 | −3.263 | 1.608 |
| Compound Example 3 | −4.881 | −3.358 | 1.523 |
| Compound Example 4 | −4.909 | −3.304 | 1.605 |
| Compound Example 5 | −4.844 | −3.233 | 1.611 |

With reference to Table 1, Model Compound Examples 1 to 5 have a HOMO which is shallower (i.e. closer to vacuum level) and a smaller band gap as to compared to Model Comparative Compounds 1 to 3.

The invention claimed is:

1. A compound of formula (I):

EAG-EDG-EAG    (I)

wherein each EAG is independently a group of formula (V):

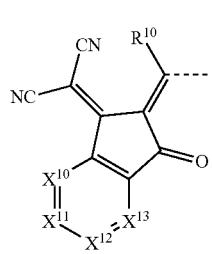

(V)

wherein $R^{10}$ in each occurrence is H or a substituent; each $X^{10}$ to $X^{13}$ is independently $CR^{13}$ or N, wherein $R^{13}$ in each occurrence is H or a substituent; and --- represents a linking position to EDG; and EDG is an electron donating group of formula (IIa):

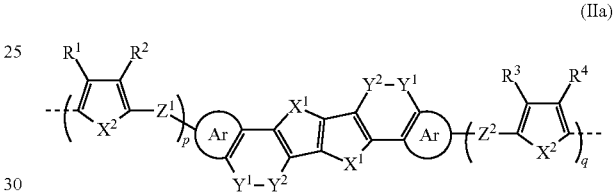

(IIa)

wherein:
each $X^1$ and $X^2$ is independently O, S or Se;
one of $Y^1$ and $Y^2$ is O and the other is $CR^5R^6$ wherein each $R^5$ and $R^6$ is independently H or a substituent;
Ar independently in each occurrence is a monocyclic or polycyclic aromatic or heteroaromatic group;
$Z^1$ is a direct bond or, together with $R^2$, forms an aromatic or heteroaromatic group $Ar^1$;
$Z^2$ is a direct bond or, together with $R^3$, forms an aromatic or heteroaromatic group $Ar^2$;
$R^1$ and $R^4$ are each independently H, a substituent or a divalent group bound to the EAG;
$R^2$ and $R^3$, independently in each occurrence is H or a substituent;
p is 0, 1, 2 or 3 and q is 0, 1, 2 or 3 with the proviso that at least one of p and q is at least 1; and
--- is a point of attachment to the EAG.

2. A compound according to claim 1, wherein the EDG is a group of formula (IIb);

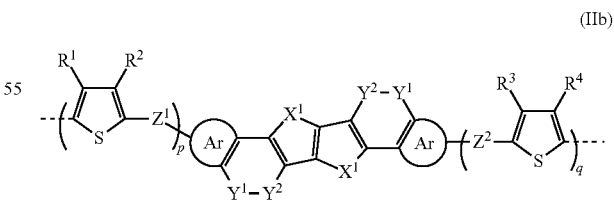

(IIb)

3. A compound according to claim 1, wherein Ar independently in each occurrence is a thiophene ring or thienothiophene ring.

4. A compound according to claim 1, wherein $Z^1$ is linked to $R^2$ to form a thiophene ring or thienothiophene ring and/or $Z^2$ is linked to $R^3$ to form a thiophene ring or thienothiophene ring.

5. A compound according to claim 1, wherein each $R^{13}$ is independently selected from H; $C_{1-12}$alkyl; and an electron withdrawing group.

6. A compound according to claim 5, wherein the electron withdrawing group is F or CN.

7. A compound according to claim 1, wherein the compound of formula (I) has formula (VII);

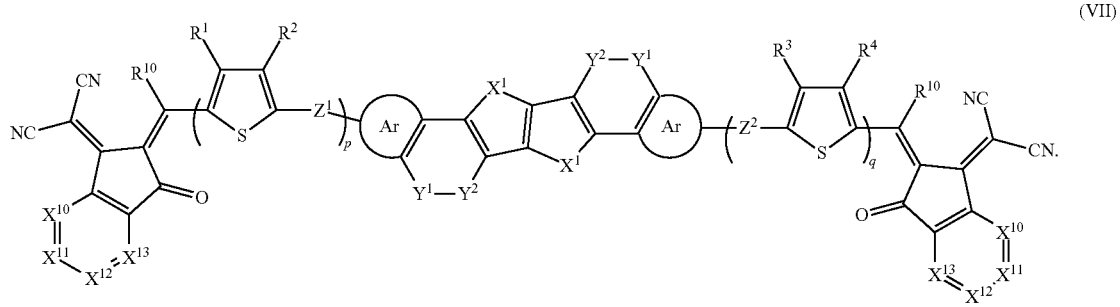

(VII)

8. The compound according to claim 1, wherein each $R^1$ to $R^4$ is independently selected from:
H;
$C_{1-12}$alkyl wherein one or more non-adjacent, non-terminal C atoms may be replaced with O, S, COO or CO; and
an aromatic or heteroaromatic group $Ar^3$ which is unsubstituted or substituted with one or more substituents.

9. A composition comprising a compound of formula (I) according to claim 1 and an electron-donating material capable of donating an electron to the compound.

10. A formulation comprising a compound or composition according to claim 9 dissolved or dispersed in one or more solvents.

11. An organic electronic device comprising a compound according to claim 1.

12. An organic photodetector comprising: an anode; a cathode; and a photosensitive organic layer disposed between the anode and cathode wherein the photosensitive organic layer comprises a composition according to claim 9.

13. A method of forming the organic photodetector according to claim 12, the method comprising formation of the photosensitive organic layer over one of the anode and cathode and formation of the other of the anode and cathode over the photosensitive organic layer.

14. A method according to claim 13 wherein formation of the photosensitive organic layer comprises deposition of a formulation between the anode and cathode and evaporation of one or more solvents.

15. A photosensor comprising a light source and an organic photodetector according to claim 12 configured to detect light emitted from the light source.

16. A photosensor according to claim 15, wherein the light source emits light having a peak wavelength greater than 750 nm.

17. A photosensor according to claim 15 configured to receive a sample in a light path between the organic photodetector and the light source.

18. A method of determining the presence and/or concentration of a target material in a sample, the method comprising illuminating the sample and measuring a response of a photodetector according to claim 12 configured to receive light emitted from the sample upon illumination.

* * * * *